United States Patent [19]
Wiggill

[11] 3,983,011
[45] Sept. 28, 1976

[54] REMOVAL OF CHLORIDE IMPURITIES FROM AN ADIPONITRILE FEED BY DISTILLATION IN THE PRESENCE OF A HIGH BOILING AMINE

[75] Inventor: John Bentley Wiggill, Hagerstown, Md.

[73] Assignee: E. I. Du Pont de Nemours and Company, Wilmington, Del.

[22] Filed: July 11, 1974

[21] Appl. No.: 487,813

[52] U.S. Cl. ................................ 203/59; 203/38; 203/91; 260/465.2; 260/465.8 R
[51] Int. Cl.$^2$ .......................................... B01D 3/34
[58] Field of Search ................. 260/465.8 R, 465.2; 203/59, 28–32, 38, 91

[56] References Cited
UNITED STATES PATENTS

| | | | |
|---|---|---|---|
| 2,570,794 | 10/1951 | Grigsey et al. | 260/465.8 R |
| 2,803,643 | 8/1957 | Halliwell | 260/465.8 R |
| 3,206,497 | 9/1965 | Oblad | 260/465.8 R |
| 3,853,947 | 12/1974 | Golser et al. | 260/465.8 R |

OTHER PUBLICATIONS

"The Condensed Chemical Dictionary", Eighth Edition; Reinhold Publishing Co.

Primary Examiner—Frank W. Lutter
Assistant Examiner—Frank Sever

[57] ABSTRACT

Process for the purification of adiponitrile containing chloride impurities by contacting said adiponitrile with a high boiling amine and recovering the purified adiponitrile containing lower amounts of chloride impurities.

5 Claims, No Drawings

REMOVAL OF CHLORIDE IMPURITIES FROM AN ADIPONITRILE FEED BY DISTILLATION IN THE PRESENCE OF A HIGH BOILING AMINE

BACKGROUND OF THE INVENTION

1. Field of the Invention

This invention relates to a process for purifying dinitriles containing chloride impurities. More specifically the process of this invention relates to a process for the purification of adiponitrile containing chloride impurities by treatment with high boiling amines.

2. Prior Art

Dinitriles are prepared by a variety of processes, for example, adiponitrile (ADN) from butadiene. One process involves the hydrocyanation of butadiene to form adiponitrile. Another process involves the chlorination of butadiene followed by treatment with a cyanide compound and hydrogenation to form adiponitrile. The crude adiponitrile prepared by such known processes is distilled to purify the adiponitrile. The purified adiponitrile can be used to prepare hexamethylene diamine which is used in the preparation of nylon. However, the adiponitrile may contain chloride impurities which adversely affect the hydrogenation catalyst activity for the preparation of hexamethylene diamine. Removal of the chloride impurities is desirable but said removal by distillation of the adiponitrile is very difficult and very expensive. U.S. Pat. No. 2,570,794 involves the separation of chlorine-containing impurities from organic nitriles by heating in the presence of benzene, water and trimethylamine or triethylamine. However, the addition of any compounds that would distill with the ADN would be very undesirable since high purity ADN is required for most applications. Thus not only do the chloride impurities adversely affect the hydrogenation catalyst activity in the preparation of hexamethylene diamine but the presence of any compound used to overcome this problem in the ADN in even small amounts will adversely affect the purity and yield of ADN.

SUMMARY OF THE INVENTION

Now it has been found that adiponitrile containing chloride impurities can be purified by a process comprising mixing the adiponitrile with a high boiling amine having an atmospheric boiling point greater than 295°C. distilling said amine and adiponitrile mixture at a temperature of about 60° to about 295°C., preferably about 200°C. and a pressure of about 0.1 mm HG to about atmospheric, preferably 50 mm HG, and recovering the pure adiponitrile containing reduced chloride impurities from the distillate.

Thus the process of the present invention is an improvement in the process of purifying crude adiponitrile containing chloride impurities by distillation, wherein the improvement is the mixing of a high boiling amine compound with the crude adiponitrile containing chloride impurities, distilling the mixture and recovering adiponitrile with lower amounts of chloride impurities from the distillate of said distillation.

The amines of the present invention include any amine or mixtures thereof that have an atmospheric boiling point greater than 295°C. Representative examples of such amines include bishexamethylenetriamine, n-pentadecylamine, n-hexadecylamine, n-heptadecylamine, di-n-octylamine, tri-n-heptylamine, 1,12-dodecamethylenediamine and 1,16-hexadecamethylenediamine.

Conveniently amines having an atmospheric boiling point greater than 295°C. are present in residue streams from the preparation of hexamethylenediamine by the catalytic hydrogenation of adiponitrile. Said residue streams comprise high boiling amine residues and adiponitrile and thus are especially advantageously used in the process of the present invention. A process stream of such high boiling residues was analyzed and found to contain (1) 6-aminocapronitrile, (2) bishexamethylenetriamine, (3) 6-aminocaproamide, (4) adiponitrile, (5) diamines with 10 carbon atoms, and (6) unknown high boilers derived from combinations of (1), (2) and (3).

The atmospheric boiling point of 6-aminocapronitrile is about 235°C.; bishexamethylenetriamine is about 325°C.; 6-aminocaproamide is about 235°C.; diamines with 10 carbon atoms are about 295° to 325°C; adiponitrile is 295°C.; and unknown high boilers described above are greater than 325°C. A typical analysis of such streams was found to be:

|     |                                                                   | Weight Percent |
| --- | ----------------------------------------------------------------- | -------------- |
| (a) | 6-aminocapronitrile                                               | 1.5–5          |
| (b) | adiponitrile                                                      | 2.5–9          |
| (c) | diamines with 10 carbon atoms                                     | 15.6–30        |
| (d) | 6-aminocaproamide                                                 | 2.5–5          |
| (e) | bishexamethylenenitamine (BHMT)                                   | 16–35          |
| (f) | unknown high boilers (UHB) derived from combination of (a), (b) and (c) | 40–60    |

The amount of high boiling amine required according to the process of the present invention is from about 100 ppm to about 10,000 ppm based on the crude adiponitrile feed stream with chloride impurities. The preferred range of said amine is about 125 ppm to about 1500 while about 500 to about 1000 ppm is most preferred. Greater than 10,000 ppm of amine, due to the concentrating effect in the distillation column, will affect the boiling point of the crude mixture in the column and could cause degradation of the adiponitrile.

The high boiling amines of this invention are surprisingly effective additives that reduce the amount of chloride impurities without deleterious effect on the ADN or hexamethylene diamine production.

The treatment of the adiponitrile to be purified with the high boiling amines of the present invention takes place in the liquid phase. The crude adiponitrile stream is mixed with the high boiling amines of the present invention and then subjected to distillation for purification. The adiponitrile to be purified containing the amine added enter the distillation column and after distillation the adiponitrile containing lower chloride impurities is recovered from the distillate. The distillation is conducted under conventional conditions for such distillations. The residue contains the high boiling amines and other compounds.

The process of the present invention is applicable to adiponitrile containing chloride impurities regardless of the process used to prepare the adiponitrile. The process of the present invention is applicable to purifying not only adiponitrile containing chloride impurities but other dinitriles containing chloride impurities. In the examples that follow adiponitrile containing chloride impurities was used to illustrate the invention. The adiponitrile used in the examples was prepared by the catalytic hydrocyanation of butadiene. A process for the preparation of adiponitrile is described in U.S. Pat. No. 3,496,216.

In the examples that follow the distillation apparatus was a glass 1-inch (I.D.) 10-plate Oldershaw distillation column equipped with automatic pressure, temperature and pot liquid level controls. The head pressure was controlled with a standard pressure regulator which maintained the desired set pressure by balancing $N_2$ pressure with vacuum from a standard oil vacuum pump. The pot temperature was controlled by a controller which maintained a set temperature and provided heat through electrical heating coils wrapped around the glass recirculating loop of the pot. The pot liquid level was controlled by monitoring the liquid level with a photo cell attached to one of the recirculating loops of the pot. When the liquid level rose or fell above a set level the photo cell would either cause a valve to open or close in the bottom of the column, thus allowing pot liquid to be removed into an evacuated tails receiver. Flow out of the overhead of the column was continuous and depended on the setting of the reflux ratio controlled by an automatic timer. The feed to the column, either just above or just below the upper or lower plates of the column, was controlled manually by means of a flow meter and a needle valve.

The distillation procedure for all the examples was as follows:

A 1-liter feed buret, maintained under atmospheric nitrogen pressure, was charged with feed liquid. In experiments where high boiling amines were added to the feed, the amine was added to the feed liquid and was stirred for several minutes before charging the 1-liter feed buret. The pot would then be evacuated, filled with feed, and distillation would be started by controlling temperature, pressure, pot liquid level and reflux ratio automatically. The feed rate would be adjusted to give desired flow rates for overhead and tails streams. Continuous distillation would continue to at least one pot residence time (pot volume/tails/vol/time). Samples of feed, overhead and tails streams would then be analyzed for concentrations of chloride.

EXAMPLE 1 — Example of crude adiponitrile (ADN) treated with 1,000 ppm diamine heels.

ADN Feed

Crude adiponitrile prepared by the process of hydrocyanation of butadiene, was combined with a high boiling amine residue (diamine heels) for three runs and compared with a run without any amine.

| Feed Solution No. | Crude ADN (grams) | Diamine Heels [1] (grams) | Diamine Heels (ppm) |
|---|---|---|---|
| 1 | No diamine heels added | | — |
| 2 | 1,890 | 1.86 | 984 |
| 3 | 1,883 | 1.85 | 984 |
| 4 | 1,910 | 1.90 | 995 |

[1] Diamine heels contained about 16–35% BHMT and 40–60% high boiling amine oligomers of BHMT and 6-aminocapronitrile.

| Column Operating Conditions (Average) | |
|---|---|
| Head Pressure | 30 mm Hg |
| Head Temperature | 185°C |
| Pot Temperature | 194°C |

| Column Operating Conditions (Average) | |
|---|---|
| Feed Rate | 153 cc/hour |
| Overhead Rate (OVHD) | 139 cc/hour |
| Tails Rate | 8 cc/hour |
| Pot Liquid Volume | 190 cc |

$$\text{Residence time} = \frac{\text{Pot Vol.}}{\text{Tails Vol/hour}} = \frac{190 \text{ cc}}{8 \text{ cc/hour}} = 23.8 \text{ hours}$$

During the first 24 hours of the experiment, feed solution No. 1 (no diamine heels added) was fed without taking any tails flow so as to concentrate the pot with respect to high boiling compounds present in the crude ADN feed. Beginning at the 24th hour a tails flow rate of 8 cc/hour was maintained. Beginning at 27.5 hours and throughout the remainder of the experiment (53 hours total time) the feed stream was changed to feed solutions numbers 2–4 which contained about 1000 ppm diamine heels. The OVHD and tails were analyzed for chloride content after between 38 to 42 hours of residence time.

Analyses for Extent of Chloride Removed

The analysis for chloride content of the samples of feed, tails and overhead streams were as follows:

The overhead and tail streams were analyzed for chloride after between 25 and 27 hours.

| Stream | Cl (ppm) | Vol. of Stream (cc) | | Density of Stream (g/cc) | | Cl(×10³) (grams) |
|---|---|---|---|---|---|---|
| Material Balance No Amine Added | | | | | | |
| Feed | 28.5 | 335 | × | 0.95 | = | 9.06 |
| OVHD | 15.5 | 331 | × | 0.95 | = | 4.88 |
| Tails | 136 | 16 | × | 0.95 | = | 2.06 |
| Material Balance With Amine | | | | | | |
| Feed | 28.5 | 612 | × | 0.95 | = | 16.5 |
| OVHD | 11* | 555 | × | 0.95 | = | 5.8 |
| Tails | 337* | 32 | × | 0.95 | = | 10.2 |

*Average of two analyses of chloride

The analytical results of Cl(ppm) in the overhead stream compared with the feed stream shows that less than half of the chloride in the feed stream appeared in the overhead stream.

EXAMPLE 2 — Example of feed material containing about 500 ppm diamine heels

Feed Material

The same source of crude adiponitrile as used in Example 1 was combined with diamine heels in two runs.

| Feed Solution (No.) | Crude ADN (grams) | Diamine Heels* (grams) | Diamine Heels (ppm) |
|---|---|---|---|
| 1 | 3736 | 1.85 | 495 |
| 2 | 1892 | 0.93 | 492 |

*Diamine heels contained about 16–35% BHMT and 40–60% high boiling amine oligomers of BHMT and 6-aminocapronitrile.

| Column Operating Conditions (average) | |
| --- | --- |
| Head Pressure | 30 mm Hg |
| Head Temperature | 185° |
| Pot Temperature | 194° |
| Feed Rate | 166 cc/hour |
| OVHD Rate | 158 cc/hour |
| Tails Rate | 7.9 cc/hour |
| Pot Liquid Volume | 190 cc |

$$\text{Residence Time} = \frac{\text{Pot. Vol.}}{\text{Tails Vol/hour}} = \frac{190 \text{ cc.}}{7.9 \text{ cc/hour}} = 24.0 \text{ hours}$$

During the first 24 hours of the experiment, crude adiponitrile (no diamine heels added) was fed without taking any tails samples. Beginning at the 24th hour and continuing through the end of the experiment (33 hours total time) the feed stream was changed to feed solutions Nos. 1 and 2 which contained about 500 ppm diamine heels. After 21.4 and 30.5 hours of operation the chloride analyses shown were made on the overhead and tail streams.

Analyses for Extent of Chloride Removed

The analyses for chloride content of the samples of feed, tails and overhead streams were as follows:

| Stream | Cl (ppm) | No. of Cl Analyses Averaged | Vol. of Stream (cc) | | Density of Stream (g/cc) | | Cl($\times 10^3$) (grams) |
| --- | --- | --- | --- | --- | --- | --- | --- |
| Feed | 28.5 | 2 | 1517 | × | 0.95 | = | 41.0 |
| OVHD | 8.6 | 5 | 1445 | × | 0.95 | = | 11.8 |
| Tails | 681 | 9 | 72 | × | 0.95 | = | 46.5 |

The analytical results for Cl(ppm) in the overhead stream compared with the feed and tails streams show that only about one-third or less of the chloride in the feed appeared in the overhead stream.

EXAMPLE 3 — Batch distillation

Batch distillation runs were made to see the effect of various levels of added high boiling amines on the extent of chloride removal from ADN. All experiments were done by charging a 500 cc. pot with premixed ADN and high-boiling amine. The pot contents were stirred by magnetic stirring bar and were heated by means of a heating mantle. The pot was connected to a glass 1-inch (ID) 10-plate Oldershaw column. The examples in the table that follows show that, under comparable conditions, the extent of chloride remaining in the pot was greater than 71% over a range of from 125 ppm to 1500 ppm of high-boiling amine or mixtures thereof.

| | | Dependence of Chloride Removal on Concentration of Added High Boiling Amine | | | | |
| --- | --- | --- | --- | --- | --- | --- |
| ADN Source | High Boiling Amine -(ppm) | Pot Temp. (°C) | Head Press. (mm Hg) | Cl (ppm) in Feed | % Liquid[1] Taken OVHD | % Cl Remaining[2] in Pot |
| Refined ADN | — | 183 | 25 | 11 | 19 | 26 |
| Refined ADN | BHMT - 500 | 205 | 37.5 | 11 | 48 | 96 |
| Refined ADN | Diamine - 500 Heels | 204 | 37.5 | 11 | 50 | 82 |
| Crude ADN | BHMT - 125 | 194 | 37.5 | 20 | 49 | 83 |
| Crude ADN | Diamine - 500 Heels | 203 | 30 | 12 | 51 | 71 |
| Crude ADN | Diamine - 1500 Heels | 205 | 37.5 | 20 | 47 | 98 |

[1] % liquid taken overhead = $\frac{\text{OVHD Vol. (cc)}}{\text{Feed Vol. (cc)}} \times 10^2$

[2] % Cl remaining in Pot = $\frac{\text{Cl (ppm)} \times \text{Vol. (cc) in Tails}}{\text{Cl (ppm} \times \text{Vol. (cc) Feed}} \times 10^2$ While certain representative embodiments and details have been shown for the purpose of illustrating the invention, it will be apparent to those skilled in this art that various changes and modifications may be made therein without departing from the spirit or scope of the invention.

I claim:

1. In a process of purifying crude adiponitrile containing chloride impurities by distillation, the improvement comprising reducing the chloride impurities by mixing the crude adiponitrile with 100–10,000 ppm of at least one amine having an atmospheric boiling point greater than 295°C. based on the crude adiponitrile feed stream to thereby form a mixture, then distilling the crude adiponitrile mixture at a temperature of about 60° to 295°C and a pressure about 0.1 mm HG to atmospheric, and recovering adiponitrile from the resultant distillate with lower amounts of chloride impurities relative to said crude adiponitrile.

2. The process of claim 1 wherein the high boiling amine is bishexamethylene triamine.

3. The process of claim 1 wherein the high boiling amine is a mixture of high-boiling amines.

4. The process of claim 1 wherein from 125–1500 ppm of said amine is used.

5. The process of claim 1 wherein from 500–1000 ppm of said amine is used.

\* \* \* \* \*